United States Patent
Koga et al.

(10) Patent No.: US 7,604,353 B2
(45) Date of Patent: Oct. 20, 2009

(54) DEFORMABLE MIRROR DEVICE AND APPARATUS FOR OBSERVING RETINA OF EYE

(75) Inventors: Akihiro Koga, Tokyo (JP); Masayuki Sekimura, Chofu (JP); Kei Masunishi, Kawasaki (JP); Akio Kobayashi, Sano (JP); Hiroyuki Kawashima, Warabi (JP); Hirotake Maruyama, Saitama (JP)

(73) Assignees: Kabushiki Kaisha Toshiba, Tokyo (JP); Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/958,725

(22) Filed: Dec. 18, 2007

(65) Prior Publication Data
US 2008/0180634 A1    Jul. 31, 2008

(30) Foreign Application Priority Data
Dec. 18, 2006  (JP)  .............................. 2006-339927

(51) Int. Cl.
*A61B 3/10* (2006.01)
*G02B 7/188* (2006.01)
*G02B 26/00* (2006.01)

(52) U.S. Cl. ..................... 351/221; 359/847; 359/295

(58) Field of Classification Search ................. 359/198, 359/212, 223, 230, 290–292, 295, 298, 846, 359/847, 872; 351/221
See application file for complete search history.

(56) References Cited

U.S. PATENT DOCUMENTS 5,223,971 A * 6/1993 Magel ........................ 359/295
2004/0201908 A1  10/2004 Kaneko

FOREIGN PATENT DOCUMENTS

JP        02-101402     4/1990
JP        2004-157527   6/2004

* cited by examiner

*Primary Examiner*—William C Choi
(74) *Attorney, Agent, or Firm*—Turocy & Watson, LLP

(57) ABSTRACT

It is made possible to improve the variations in the "generated force (load)—deflection characteristics". A deformable mirror device includes: a substrate; a plurality of electrodes provided on the substrate; a spacer disposed on the substrate; a support member disposed above the spacer and having an opening passing through from a first face of the support member facing to the substrate to a second face of the support member facing opposite from the first face; a first insulation film provided on the first face of the support member; a second insulation film provided on the second face of the support member; and a deformable electrode film disposed so as to be opposed to the electrodes at a spacing, formed so as to cover the opening, and supported by the support member with sandwiching the first insulation film. The electrode film includes a reflection portion on a face opposite from the electrodes, and the support member is disposed on the substrate with sandwiching the electrode film, the first insulation film and the spacer.

7 Claims, 5 Drawing Sheets

CONVEX DOWNWARD BY APPROXIMATELY 50 μm

SiO2 ON ONE SIDE (THERMAL OXIDATION)

MEASURENET POSITION[mm]

DEFORMABLE MIRROR DEVICE AND APPARATUS FOR OBSERVING RETINA OF EYE

CROSS-REFERENCE TO RELATED APPLICATION

This application is based upon and claims the benefit of priority from prior Japanese Patent Application No. 2006-339927 filed on Dec. 18, 2006 in Japan, the entire contents of which are incorporated herein by reference.

BACKGROUND OF THE INVENTION

1. Field of the Invention

The present invention relates to a deformable mirror device and an apparatus for observing retina of eye.

2. Related Art

In general, an apparatus for observing retina of eye is an apparatus which irradiates a retina of an eye to be examined with illumination light and receive and detect light of an image of the retina to be examined through an retina image forming optical system by using an image pickup device (for example, a CCD camera) in order to observe the retina of the eye. For detecting and preventing a disease concerning eyes, it is desirable that the detection accuracy and resolution are high as far as possible. Since an eyeball is not an ideal lens having no aberration, however, the eyeball has a wavefront aberration which becomes a factor of lowering the detection accuracy and resolution.

Therefore, a deformable mirror which can vary its surface shape on the basis of information supplied from a controller is provided between the image pickup device which detects the image of the retina and the retina of the eye to be examined. The image of the retina of the eye to be examined reflected by the deformable mirror is led to a wavefront sensor (for example, the Shack Hartmann sensor) to detect wavefront aberration. A control device indicates a displacement quantity to the deformable mirror so as to reduce or eliminate the wavefront aberration on the basis of the detected wavefront aberration. Owing to this indication, the shape of the deformable mirror is deformed and an image having no wavefront aberration is obtained by the image pickup device.

A deformable mirror having a shape variable by electrostatic sucking force is known (see, for example, FIG. 2 in JP-A 02-101402 (KOKAI)). The deformable mirror shown in FIG. 2 in JP-A 02-101402 (KOKAI) has a configuration obtained by forming a fixed electrode film 12 on an insulative substrate 11, a spacer part 18 having an opening in the center on the fixed electrode film 12, stacking a reflection film 17, a movable electrode film 16 and a SiO$_2$ insulation film 14 on the spacer part 18 so as to cover the opening, and forming a silicon substrate 13 having an opening in the center on the stacked film. Therefore, the stacked film consisting of the reflection film 17, the movable electrode film 16 and the SiO$_2$ insulation film 14 is disposed as a membrane part having a peripheral part fixed by the spacer part 18 and the silicon substrate 13 and a central part deformable by electrostatic force between the fixed electrode 12 and the movable electrode film 16.

In the membrane part, it is desirable that "generated force (load)—deflection characteristics" obtained when a predetermined voltage is applied between the fixed electrode and the movable electrode are uniform and symmetric in the plane as far as possible and their variations in manufacturing of the deformable mirror are small. This is because if there are variations it is necessary to execute adjustment work according to individual characteristics.

If the "generated force (load)—deflection characteristics" have a property that the membrane part tends to harden, then a greater voltage is needed to generate the same displacement. This can be a cause of hampering the fealizability and usefulness of a drive circuit and a peripheral circuit of the deformable mirror.

The "generated force (load)—deflection characteristics" are influenced by various causes. In the deformable mirror, however, residual stress remaining in a thin film or the like caused by difference in coefficient of linear thermal expansion between substances used as materials exerts a great influence. Furthermore, the "generated force (load)—deflection characteristics" depend on material characteristics (such as the Young's modulus and Poisson's ratio) of members used in the membrane part, flexural rigidity determined by characteristics (second moment of area) concerning the shape, and boundary conditions in regions for fixing or supporting peripheries of the membrane part. Residual stress remaining in the thin film or the like exerts an influence upon the above-described boundary conditions.

In the deformable mirror described in JP-A 02-101402 (KOKAI), except for the reflection film, the membrane part is a stacked film consisting of the movable electrode film 16 and the SiO$_2$ insulation film 14, and the membrane part has a configuration fixed in its peripheries by the spacer part 18 and the silicon substrate 13. Therefore, the "generated force (load)—deflection characteristics" in the membrane part vary and have anisotropy (nonuniformity) in the plane, under the influence of the deflection in the region fixing the membrane part exerting upon the boundary conditions at a fixed point and the influence of the residual stress existing within the movable electrode film 16 and the insulation film 14 laminated in the membrane part. The above-described deflection is generated by the difference in coefficient of linear thermal expansion between the constituent films. As for the residual stress, the magnitude and the direction (tension/compression) of the residual stress are influenced by the process kind and procedure at the time of film forming.

The degree of influence of the residual stress and the boundary conditions upon the "generated force (load)—deflection characteristics" is very large. A small difference in the residual stress or the boundary conditions causes a great difference in an output result (the deflection quantity of the membrane). The design work concerning the structure of the membrane part and the arrangement and shape of electrodes provided on the substrate surface is complicated.

SUMMARY OF THE INVENTION

The present invention has been made in view of these circumstances, and an object thereof is to provide a deformable mirror device capable of improving the variations in the "generated force (load)—deflection characteristics" and an apparatus for observing retina of eye including the mirror.

A deformable mirror device according to a first aspect of the present invention includes: a substrate; a plurality of electrodes provided on the substrate; a spacer disposed on the substrate; a support member disposed above the spacer and having an opening passing through from a first face of the support member facing to the substrate to a second face of the support member facing opposite from the first face; a first insulation film provided on the first face of the support member; a second insulation film provided on the second face of the support member; and a deformable electrode film disposed so as to be opposed to the electrodes at a spacing, formed so as to cover the opening, and supported by the support member with sandwiching the first insulation film, wherein the electrode film includes a reflection portion on a face opposite from the electrodes, and the support member is disposed on the substrate with sandwiching the electrode film, the first insulation film and the spacer.

An apparatus for observing retina of eye according to a second aspect of the present invention includes: a retina illumination system illuminating a retina of an eye to be examined with illumination light to observe the retina; a compensation optical portion comprising the deformable mirror device according to the first aspect, and correcting a reflected image obtained from the retina by the illumination light of the retina illumination system by changing a shape of the deformable mirror device according to a given correction quantity; a retina image forming optical system receiving light of the retina image corrected by the compensation optical portion and forming an retina image; and a retina image light receiving portion receiving light of the retina image formed by the retina image forming optical system.

DESCRIPTION OF THE EMBODIMENTS

Hereafter, embodiments of the present invention will be described with reference to the drawings.

First Embodiment

Figure 1A:
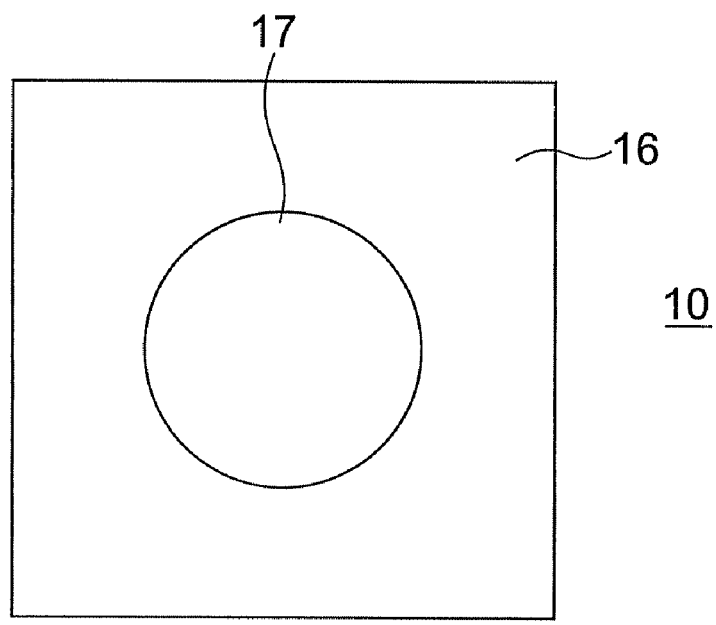
FIG. 1A is a plan view of a deformable mirror device according to a first embodiment.
Figure 1B:
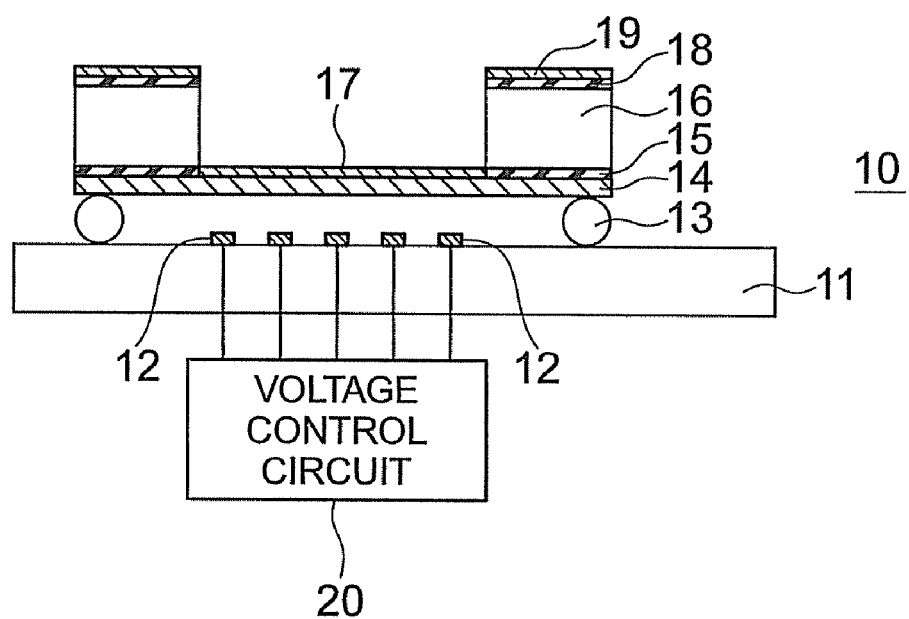
FIG. 1B is a cross sectional view of the deformable mirror device according to the first embodiment.

A deformable mirror device according to a first embodiment of the present invention is shown in FIGS. 1A and 1B. FIG. 1A is a plan view of the deformable mirror device according to the present embodiment. FIG. 1B is a cross sectional view of the deformable mirror device according to the present embodiment. In FIG. 1A, an insulation film 18 and a metal thin film 19 described later are omitted.

In a deformable mirror device 10 according to the present embodiment, a plurality of electrodes 12 are provided, for example, in a central portion on a printed circuit board 11. A support member 16 having an opening in the center is provided over the printed circuit board 11 via a spacer 13 disposed on the printed circuit board 11. An insulation film 15 formed of, for example, $SiO_2$ is provided on the face of the support member 16 opposite from the printed circuit board 11. An electrode film 14 is provided on the face of the insulation film 15 opposed to the printed circuit board 11 so as to cover the opening of the support member 16. This electrode film 14 is supported by the support member 16 via the insulation film 15. A reflection film 17 (reflector) is provided in a region Which is located on the face of the electrode film 14 opposite from the electrodes 12 and superposed on the opening of the support member 16. The electrode film 14 and the reflection film 17 constitute the membrane portion which can be deformed. Furthermore, an insulation film 18 formed of, for example, $SiO_2$ is provided on the face of the support member 16 opposite from the face opposed to the printed circuit board 11. A metal thin film 19 formed of the same material as that of the reflection film 17 is provided on the insulation film 18.

The electrodes 12 are connected to a voltage control circuit 20, and the electrode film 14 is grounded. If a voltage from the voltage control circuit 20 is applied to the electrodes 12, the electrostatic force is exerted between the electrodes 12 and the electrode film 14 and the electrode film 14 deflects. When a voltage is not applied between the electrodes 12 and the electrode film 14, therefore, the electrode film 14 is disposed at constant spacing from the electrodes 12.

In the deformable mirror device according to the present embodiment having the above-described configuration, the reflection film 17 and the electrode film 14 are formed in the membrane portion. In the present embodiment, the electrode film 14 is formed of a conductive silicon film with impurities introduced as described later. Therefore, it is possible to suppress residual stress generation in the electrode film 14 included in the membrane portion. Furthermore, since the membrane portion is fixed to the support member 16 via the insulation film 15, deflections at the fixed ends become uniform. As a result, variations of the "generated force (load)—deflection characteristics" can be improved.

In the deformable mirror device according to the present embodiment having the above-described configuration, the membrane portion has the electrode film 14 and the reflection film 17. In the present embodiment, the electrode film 14 is formed of a conductive silicon film with impurities introduced as described later. Therefore, it is possible to suppress residual stress generation in the electrode film 14 included in the membrane portion. Since the membrane portion is fixed to the support member 16 via the insulation film 15, deflections at the fixed ends become uniform. As a result, variations of the "generated force (load)—deflection characteristics" can be improved.

In the present embodiment, insulation films provided on and under the support member 16 are $SiO_2$ films. However, the insulation films are not restricted to $SiO_2$ films. Films of different materials but with the same film thickness may be provided on and under the support member 16 by using the same manufacturing method as long as the films have nearly equal coefficients of linear expansion.

Figure 2A:
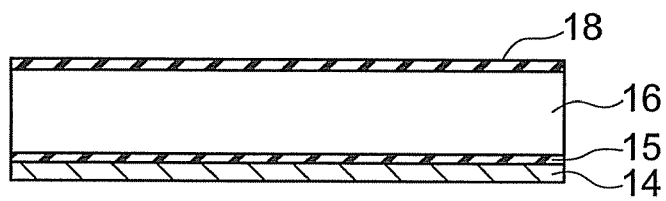
FIGS. 2A to 2G are cross sectional views showing manufacturing processes of the deformable mirror device according to the first embodiment.
Figure 2B:
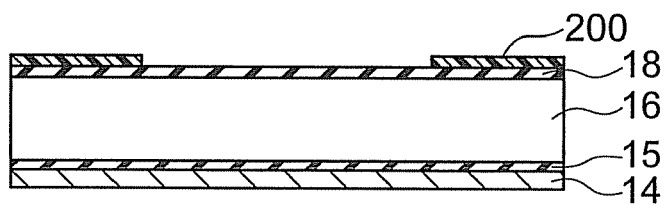

A manufacturing method of the deformable mirror device according to the present embodiment will now be described with reference to FIGS. 2A to 2G. First, an SOI (Silicon On Insulator) wafer including $SiO_2$ films 15 and 18 having the same film thickness on and under the support substrate 16 formed of Si is prepared as shown in FIG. 2A. Typically, as for the SOI wafer, a single crystal Si wafer is prepared and a $SiO_2$ film is generated on the whole wafer face (both the obverse and reverse) by a thermal oxidation furnace or the like (the film thickness on the obverse is the same as that on the reverse). Thereafter, another single crystal Si wafer is bonded via the $SiO_2$ film. After the bonding, one of bonded single crystal Si wafers is made thin by a polishing process until a desired thickness is attained. As a result, an SOI wafer having a four-layer structure with "the thermally oxidized $SiO_2$ film 18/the single crystal Si layer 16/the thermally oxidized $SiO_2$ film 15/the single crystal Si layer 14" is obtained. By the way, high concentration impurities are introduced into the single crystal Si layer 15 and it is used as an electrode film.

Subsequently, a photoresist is applied to the surface of the SOI wafer (onto the SiO$_2$ film 18), and exposure and development are conducted on the photoresist. As a result, a resist pattern 200 having an opening in the center is formed (see FIG. 2B).

Figure 2C:
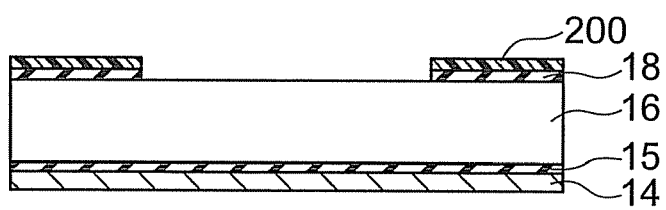
Figure 2D:
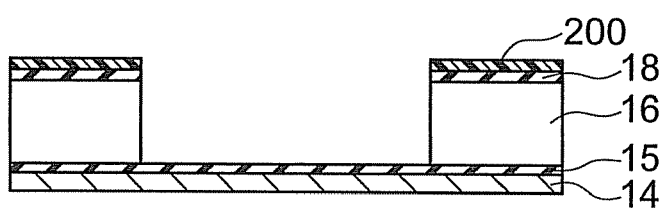
Figure 2E:
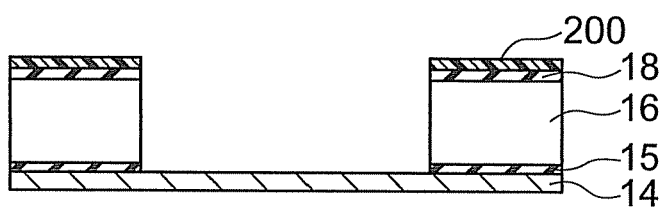
Figure 2F:
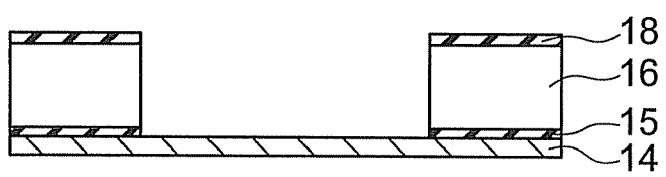

Subsequently, as shown in FIG. 2C, the thermally oxidized SiO$_2$ film 18 is patterned by using the resist pattern 200 as a mask. As an etchant, a diluted fluoric acid or ammonium fluoride aqueous solution is used. Subsequently, as shown in FIG. 2D, the single crystal Si layer 16 is patterned by dry etching process using Deep-RIE (Reactive Ion Etching) and by using the resist pattern 200 and the patterned thermally oxidized SiO$_2$ film 18 as masks. This patterning is conducted until the thermally oxidized SiO$_2$ film 15 is exposed. In other words, the patterning of the single crystal Si layer 16 is conducted by using the thermally oxidized SiO$_2$ film 15 as an etch stop layer. Thereafter, the thermally oxidized SiO$_2$ film 15 which exists in the membrane portion is removed by etching (see FIG. 2E). Thereafter, the resist pattern 200 is exfoliated (see FIG. 2F).

Figure 2G:
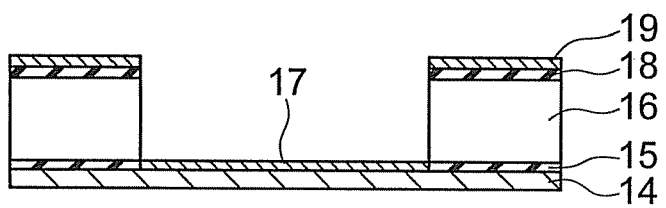

By the processes heretofore described, the deformable mirror structure with the SiO$_2$ film 15 removed except the connection portion between the membrane portion and the single crystal Si layer 16 can be obtained. Thereafter, in order to obtain optical reflection characteristics, a metal thin film (such as an Al film) 17 is formed on the reflection face side of the membrane portion (in an evaporation process or the like) as shown in FIG. 2G, and finally a SiO$_2$ thin film which is not illustrated is formed as a protection film functioning as a countermeasure against cracks and contamination to complete the deformable mirror. Although the metal thin film 19 is formed on the surface of the single crystal Si layer 16 as well via the insulating film 18 in this manufacturing method, it may not be formed.

Results of influence of residual stress exerting on the deflection of the Si substrate will now be described with reference to FIGS. 3A to 4B as to the case where the thermally oxidized SiO$_2$ film is formed on both sides of the Si substrate as in the present embodiment and the case where the thermally oxidized SiO$_2$ film is formed on one side of the Si substrate as in the comparative example.

Figure 4A:
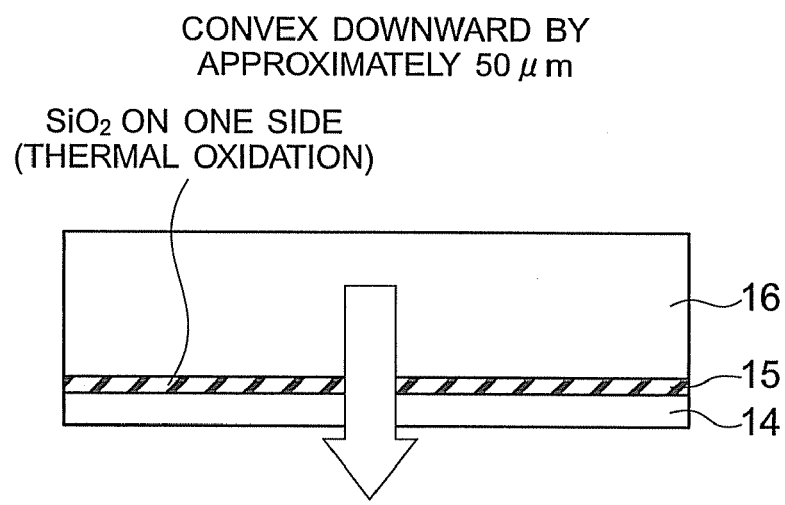
FIGS. 4A and 4B are diagrams for explaining deflection characteristics of a deformable mirror according to a comparative example.
Figure 4B:
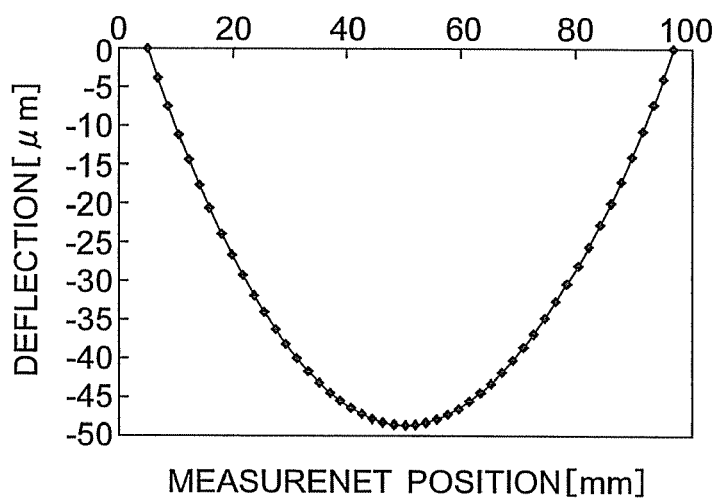

The Si substrate used has a diameter of 6 inches. In the comparative example, the thermally oxidized SiO$_2$ film 15 exists only between the Si substrate 16 and the displacing membrane portion 14 as shown in FIG. 4A. In that case, the membrane portion 14 deflects so as to take a convex shape downward (indicated by an arrow in FIG. 4A) and the maximum value of the deflection is approximately 50 µm (see FIG. 4B).

Figure 3A:
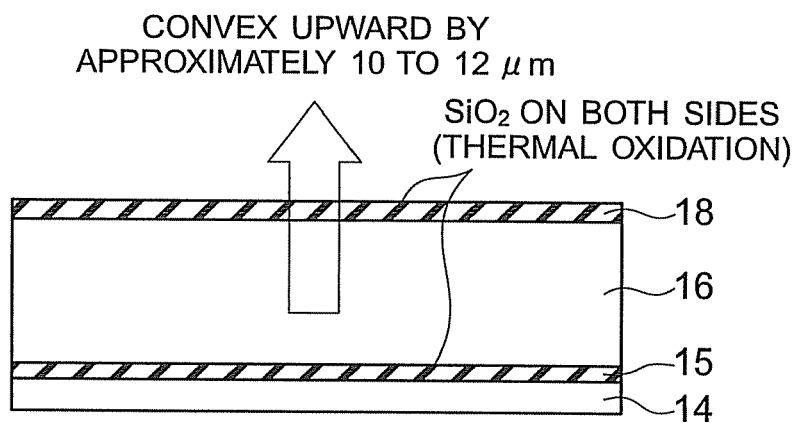
FIGS. 3A and 3B are diagrams for explaining deflection characteristics of a deformable mirror according to the first embodiment.
Figure 3B:
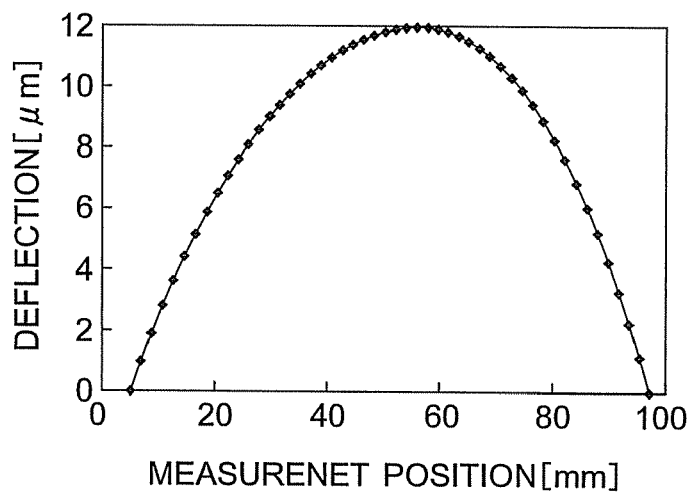

On the other hand, if the thermally oxidized SiO$_2$ films 15 and 18 of the same kind and film thickness are provided on and under the Si substrate surfaces as in the present embodiment shown in FIG. 3A, then the membrane part 14 deflects so as to take a convex shape upward (indicated by an arrow in FIG. 3A) and the maximum value of the deflection is in the range of approximately 10 µm to 12 µm (see FIG. 3B). It is understood that the deflection characteristics have been improved by providing thermally oxidized SiO$_2$ film on both sides of the Si substrate.

According to the present embodiment, variations of the "generated force (load)—deflection characteristics" can be improved as heretofore described.

For using the printed circuit board 11 as the electrode substrate 11 of the deformable mirror device, it is necessary to conduct smoothing following a face of a metal plate so as to make the flatness of the surface approximately several µm. If the printed circuit board is used as the electrode substrate 11 of the deformable mirror, the deformable mirror can be manufactured at a comparatively low cost. By utilizing a multilayer printed circuit board as the electrode substrate 11, it becomes possible to cope with the drive voltage applied to the electrodes becoming higher and fine membrane shape control due to increase in the number of electrodes.

Second Embodiment

An apparatus for observing retina of eye according to a second embodiment of the present invention will now be described.

Figure 5:
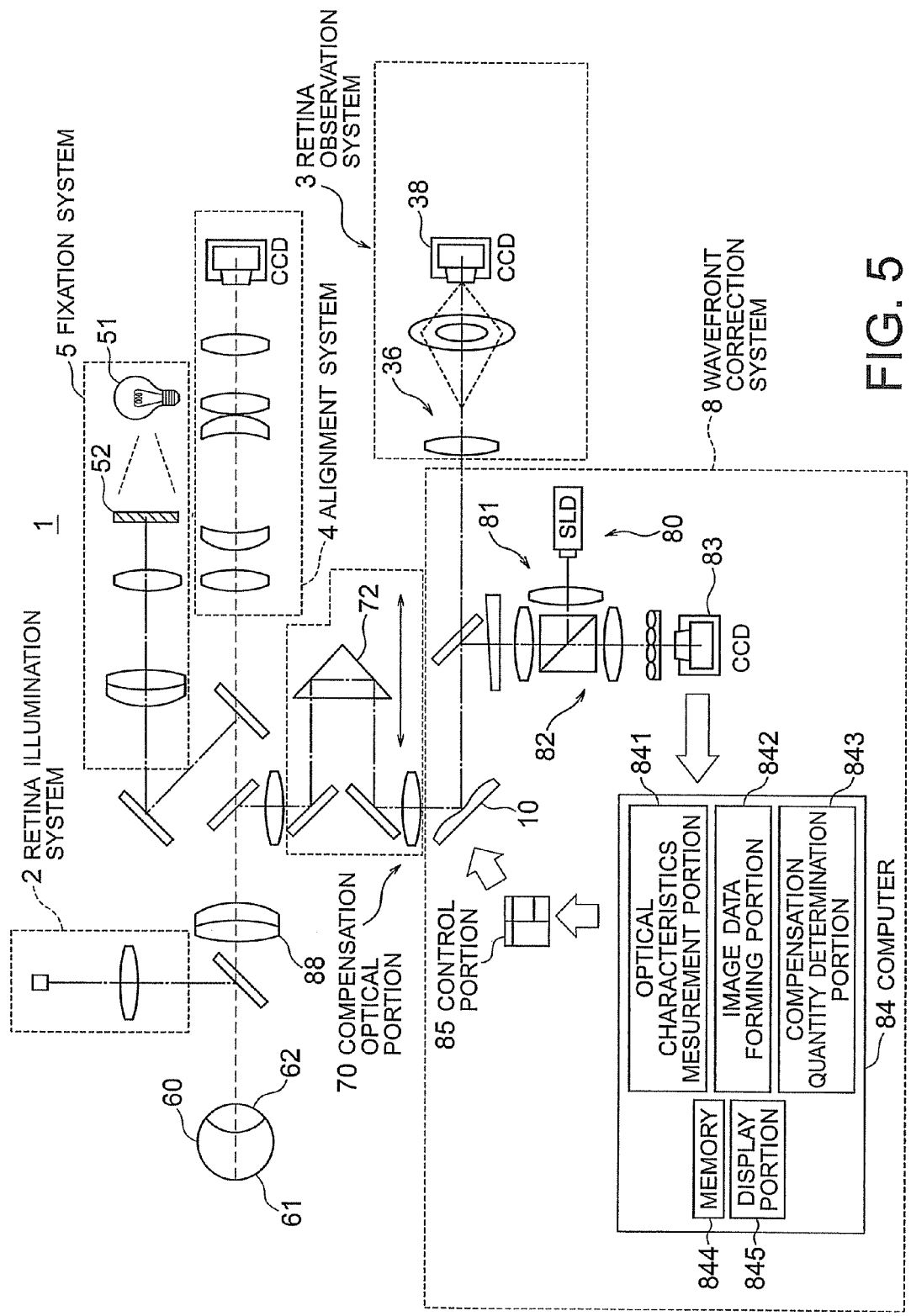
FIG. 5 is a block diagram showing a schematic configuration of an apparatus for observing retina of eye according to a second embodiment.

The apparatus for observing retina of eye according to the present embodiment includes the deformable mirror device 10 according to the first or second embodiment. A schematic configuration of the apparatus for observing retina of eye according to the present embodiment is shown in FIG. 5. An apparatus for observing retina of eye 1 according to the present embodiment includes a wavefront correction system 8, a retina illumination system 2, a retina observation system 3, an alignment system 4, a fixation system 5 and a compensation optical portion 70. The wavefront correction system 8 includes a wavefront measurement system 80, a computer 84 and a control portion 85. The wavefront measurement system 80 includes a point projection optical system 81, a point light receiving optical system 82 and a point light receiving portion 83 (CCD). The computer 84 includes an optical characteristics measurement portion 841, an image data forming portion 842, a compensation quantity determination portion 843, a memory 844 and a display portion 845.

The retina illumination system 2 includes a second light source portion, a condenser lens and a beam splitter. The retina illumination system 2 is provided to illuminate a predetermined region on a retina of an eye to be examined with a second luminous flux emitted from the second light source portion. The retina observation system 3 includes a retina image forming optical system 36 and a retina image light receiving portion 38 (CCD). The retina image forming optical system 36 includes, for example, an afocal lens 88, the compensation optical portion 70, a condenser lens and a beam splitter. The retina image forming optical system 36 leads light reflected by a retina 61 to the retina image light receiving portion 38 via the compensation optical portion 70. The compensation optical portion 70 includes the deformable mirror device 10 which compensates aberration of measured light and a moving prism and a spherical lens which move in the optical axis direction and compensate spherical components. The compensation optical portion 70 is disposed in the point projection optical system 81 and the retina image forming optical system 36, and the compensation optical portion 70 compensates, for example, aberration of the returning reflected luminous flux reflected by the eye 60 to be examined.

The alignment system 4 includes a condenser lens and an alignment light receiving portion, and leads luminous flux emitted from the light source portion, reflected by cornea 62 of the eye 60 to be examined and returning to an alignment light receiving portion. The fixation system 5 includes an optical path which projects a fixation point for fixation or fogging of the eye 60 to be examined, and includes a third light source portion 51, a fixation index 52 and relay lenses. The eyeground 61 can be illuminated from the fixation index 52 by using luminous flux emitted from the third light source portion 51, and the eye 60 to be examined is caused to observe an image of the fixation index 52.

The optical characteristics measurement portion 841 determines optical characteristics including higher order aberration of the eye 60 to be examined on the basis of an output from the point light receiving portion 83. The image data forming portion 842 conducts simulation as to how the fixation index is seen on the basis of optical characteristics and calculates simulation image data or examined eye data such as the MTF showing how the fixation index is seen. The memory 844 stores a plurality of voltage change templates for adjusting the deformable mirror 10. The compensation quantity determination part 843 selects a voltage change template stored in the memory 844, determines a correction quantity of the deformable mirror 10 on the basis of the selected voltage change template, and outputs the correction quantity to the control portion 85. The control portion 85 deforms the deformable mirror device 10 on the basis of an output of the compensation quantity determination portion 843.

The apparatus for observing retina of eye according to the present embodiment has effects described hereafter. Reflected light from the retina of the eye 60 to be examined contains aberration because the eye optical system is not ideal and a clear retina image is not obtained. In the current retina camera, therefore, cylinder components (Zernike (2, ±2) components) are corrected by inserting a correction cylinder lens in the optical path. As for the refraction degree intervals of the cylinder lens, however, there is a limitation of certain constant intervals (for example, 3 D (diopter) intervals). A clear retina image subjected to sufficient aberration correction cannot be obtained. The optical distortion can be corrected by using the deformable mirror device 10. If the distance between the membrane portion and the electrodes is made large and the deformable mirror device 10 is driven with a high drive voltage, a large aberration quantity capable of covering the refraction degree interval of the cylinder lens can be corrected. Furthermore, a complicated aberration can be corrected by increasing the number of electrodes under the membrane portion.

According to the embodiments of the present invention, variations of the "generated force (load)—deflection characteristics" can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

What is claimed is:

1. A deformable mirror device comprising:
   a substrate;
   a plurality of electrodes provided on the substrate;
   a spacer disposed on the substrate;
   a support member disposed above the spacer and having an opening passing through from a first face of the support member facing to the substrate to a second face of the support member facing opposite from the first face;
   a first insulation film provided on the first face of the support member;
   a second insulation film provided on the second face of the support member; and
   a deformable electrode film disposed so as to be opposed to the electrodes at a spacing, formed so as to cover the opening, and supported by the support member with sandwiching the first insulation film,
   wherein the electrode film comprises a reflection portion on a face opposite from the electrodes, and the support member is disposed above the substrate with sandwiching the electrode film, the first insulation film and the spacer, and wherein
   the support member comprises silicon,
   the first and second insulation films comprise silicon oxide, and
   the electrode film comprises a silicon film with impurities introduced therein.

2. The device according to claim 1, wherein the first insulation film and the second insulation film have the same film thickness.

3. The device according to claim 1, wherein the substrate is a printed circuit board.

4. An apparatus for observing retina of eye comprising:
   a retina illumination system illuminating a retina of an eye to be examined with illumination light to observe the retina;
   a compensation optical portion comprising the deformable mirror device according to claim 1, and correcting a reflected image obtained from the retina by the illumination light of the retina illumination system by changing a shape of the deformable mirror device according to a given correction quantity;
   a retina image forming optical system receiving light of the retina image corrected by the compensation optical portion and forming an retina image; and
   a retina image light receiving portion receiving light of the retina image formed by the retina image forming optical system.

5. The apparatus according to claim 4, wherein the first insulation film and the second insulation film have the same film thickness.

6. The apparatus according to claim 4, wherein
   the support member comprises silicon,
   the first and second insulation films comprise silicon oxide, and
   the electrode film comprises a silicon film with impurities introduced therein.

7. The apparatus according to claim 4, wherein the substrate is a printed circuit board.

* * * * *